United States Patent [19]

McGredy

[11] Patent Number: Plant 6,263

[45] Date of Patent: Aug. 30, 1988

[54] ROSE PLANT NAMED MACDEEPO

[76] Inventor: Samuel D. McGredy, 130 B Beach Road, Castor Bay, Auckland 9, New Zealand

[21] Appl. No.: 895,305

[22] Filed: Aug. 11, 1986

[51] Int. Cl.[4] ..... A01H 5/00

[52] U.S. Cl. ..... Plt./15

[58] Field of Search ..... Plt./15

*Primary Examiner*—Robert E. Bagwill

*Attorney, Agent, or Firm*—Vincent G. Gioia

[57] ABSTRACT

A new Naples yellow hybrid tea rose variety.

1 Drawing Sheet

The present invention relates to a new and distinct variety of rose plant of the hybrid tea rose class, which was originated by my crossing as seed parent an unnamed, unpatented seedling of my creation and as pollen parent the rose known as "Mabella" (U.S. Plant Pat. No. 3,228). The denomination of this new rose is "MacDeepo".

Among the novel characteristics possessed by this new variety which distinguish it from its parents and all other varieties of which I am aware are its Naples yellow colored flowers which are attractively displayed against shiny dark green foliage and which are long lasting on the plant and after cutting. Asexual reproduction by budding of the new variety as performed in Clackamas County, Oreg. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "11A" is plate 11A of The Royal Horticultural Society Colour Chart.

Parentage: Seedling.
*Seed parent.*—Unnamed seedling.
*Pollen parent.*—"Mabella".
Class: Hybrid Tea.

The following observations are made of specimens grown outdoors in Clackamas County, Oreg., during the month of September.

FLOWER

Blooming habit: Continuous.

A. Bud:
(1) *Size.*—Medium.
(2) *Form.*—Long pointed.
(3) *Color.*—As sepals divide, buds are near 11A.
(4) *Sepals.*—Long, simple, glaborous.
(5) *Peduncle.*—Length — average. Aspect — straight. Strength — erect. Color — green.

B. Bloom:

(1) *Size.*—Average size when fully expanded — about 4 inches.
(2) *Borne.*—Singly, one to a stem.
(3) *Form.*—High centered, pointed bud. Outer petals reflex and quill to points; inner petals roll under.
(4) *Petalage.*—Number of petals under normal conditions — about 24.
(5) *Color.*—As petals unfurl, flower coloring becomes Naples yellow 11A to 11D with outer petals having the lighter tonality. Petal undersurface has deeper yellow tones at lower petal segments. Some veining and mixed yellow tone washing also appears on some petals.

C. Petals
(1) *Texture.*—Thick.
(2) *Appearance.*—Inside satiny and outside satiny.
(3) *Form.*—Broad, fan shaped.
(4) *Arrangement.*—Regularly arranged.
(5) *Petaloids in center.*—Few.
(6) *Persistence.*—Drop off cleanly.
(7) *Fragrance.*—Slight.
(8) *Lasting quality.*—Very long lasting quality on plant and as cut flower.

REPRODUCTIVE ORGANS

A. Stamens, filaments and anthers:
*Arrangement and color.*—Irregular. Color — filaments near 14A.

B. Pollen:
*Color.*—Near 17A.

C. Styles: Many, long, thin, hairy.

D. Stigmas:
*Color.*—Near 14C.

E. Hips: None observed.

PLANT

A. Form: Upright.

B. Growth: Vigorous.
*Height attained.*—About 6 feet.

C. Foliage: Compound 5 leaflets.
(1) *Size.*—Medium.
(2) *Quantity.*—Abundant.
(3) *Color.*—New foliage: Upper side — near 185B. Under side — near 185C. Old foliage: Upper side — near 133A. Under side — near to 133B.
(4) *Shape.*—Oval, acuminate.
(5) *Texture.*—Upper side is leathery; under side is glaborous.
(6) *Edge.*—Serrate.
(7) *Serration.*—Ordinary.

(8) *Leaf stem.*—Color — near to 200C. Under side — near 147C.

(9) *Stipules.*—Short, simple.

(10) *Resistance to disease.*—Blackspot — excellent. Mildew — average. Rust — excellent.

D. Wood:

(1) *New wood.*—Color — near 187B. Bark — smooth.

(2) *Old wood.*—Color — near 137C. Bark — smooth.

E. Thorns:

(1) *Thorns.*—Quantity (main stalk) — few. On laterals from stalk — few. Form — long, slightly curved. Length — long. Color — near 183A. Position — irregular.

(2) *Prickles.*—None.

F. Winter hardiness: Needs protection.

I claim:

1. A new and distinct variety of rose plant of the hybrid tea rose class, substantially as shown and described, characterized particularly by Naples yellow colored flowers attractively displayed against shiny dark green foliage and which are long lasting on the plant and as cut flowers.

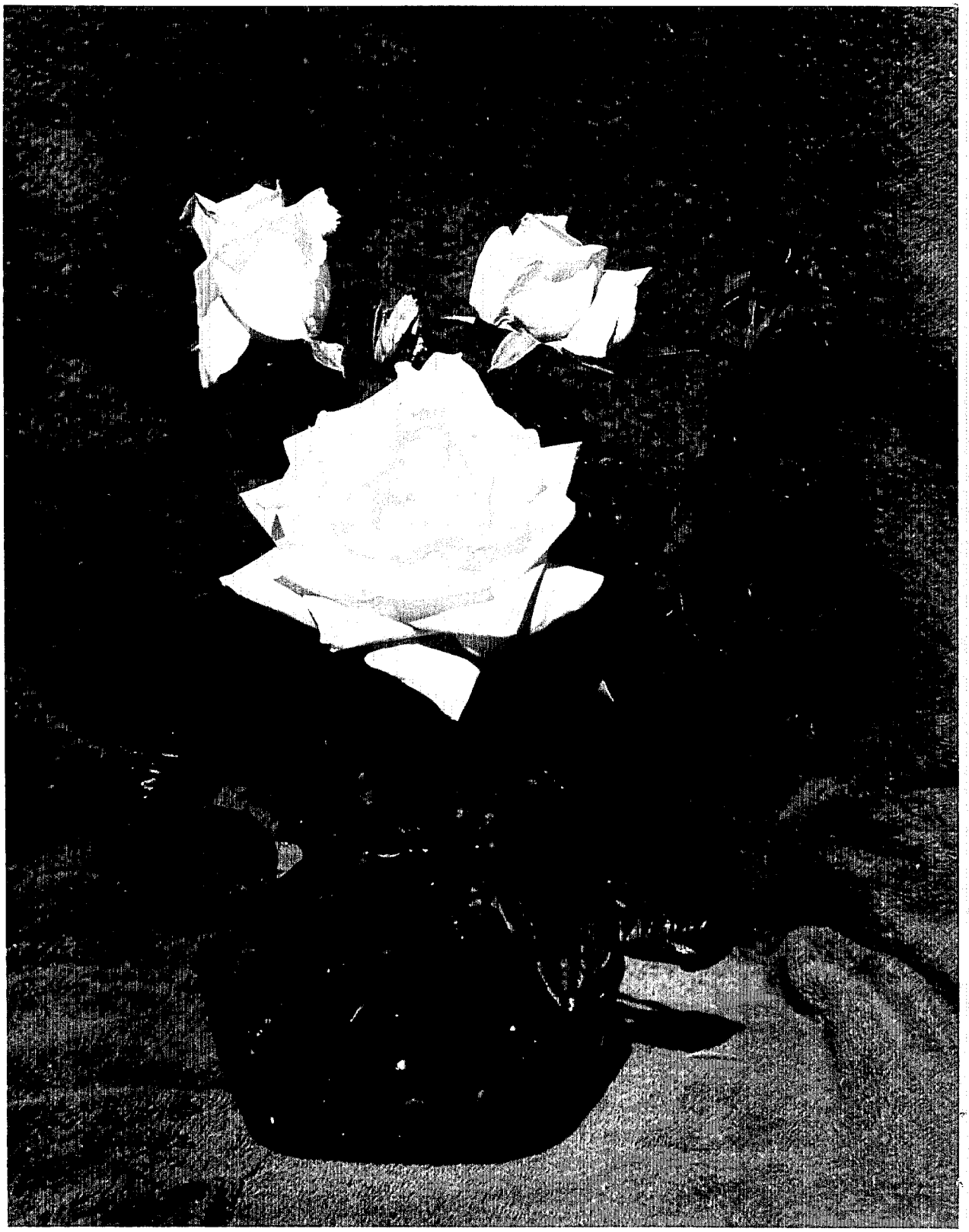

* * * * *